United States Patent
Patangay et al.

(10) Patent No.: US 7,957,802 B2
(45) Date of Patent: Jun. 7, 2011

(54) METHOD, APPARATUS, AND SYSTEM TO OPTIMIZE CARDIAC PRELOAD BASED ON MEASURED PULMONARY ARTERY PRESSURE

(75) Inventors: Abhilash Patangay, Inver Grove Heights, MN (US); Jiang Ding, Shoreview, MN (US); Jonathan T. Kwok, Denville, NJ (US); Barun Maskara, Blaine, MN (US); Yinghong Yu, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 647 days.

(21) Appl. No.: 11/894,082

(22) Filed: Aug. 20, 2007

(65) Prior Publication Data
US 2009/0054945 A1 Feb. 26, 2009

(51) Int. Cl.
*A61N 1/362* (2006.01)
(52) U.S. Cl. .................... 607/23
(58) Field of Classification Search .......... 607/23
See application file for complete search history.

(56) References Cited

U.S. PATENT DOCUMENTS

| | | | |
|---|---|---|---|
| 4,674,518 A | 6/1987 | Salo | |
| 4,686,987 A | 8/1987 | Salo et al. | |
| 5,334,222 A | 8/1994 | Salo et al. | |
| 5,417,717 A | 5/1995 | Salo et al. | |
| 5,466,245 A | 11/1995 | Spinelli et al. | |
| 5,487,752 A | 1/1996 | Salo et al. | |
| 5,601,613 A | 2/1997 | Florio et al. | |
| 5,626,623 A * | 5/1997 | Kieval et al. ............ | 607/23 |
| 5,700,417 A | 12/1997 | Fernyhough | |
| 5,800,464 A | 9/1998 | Kieval | |
| 6,141,590 A | 10/2000 | Renirie et al. | |
| 6,144,800 A | 11/2000 | Kobayashi | |
| 6,144,880 A | 11/2000 | Ding et al. | |
| 6,221,011 B1 | 4/2001 | Bardy | |
| 6,270,457 B1 | 8/2001 | Bardy | |
| 6,277,072 B1 | 8/2001 | Bardy | |
| 6,280,380 B1 | 8/2001 | Bardy | |
| 6,312,378 B1 | 11/2001 | Bardy | |
| 6,336,903 B1 | 1/2002 | Bardy | |
| 6,358,203 B2 | 3/2002 | Bardy | |
| 6,368,284 B1 | 4/2002 | Bardy | |
| 6,371,922 B1 | 4/2002 | Baumann et al. | |
| 6,398,728 B1 | 6/2002 | Bardy | |

(Continued)

OTHER PUBLICATIONS

Nakamoto et al., "Variability of Ventricular Excitation Interval Does Not Reflect Fluctuation in Atrial Excitation Interval during Exercise in Humans: AV Nodal Function as Stabilizer", J. Physiol. Sci., vol. 56, No. 1, Feb. 2006, pp. 67-77.

(Continued)

*Primary Examiner* — Carl H Layno
*Assistant Examiner* — Jeremiah T Kimball
(74) *Attorney, Agent, or Firm* — Hollingsworth & Funk, LLC

(57) ABSTRACT

Optimizing cardiac preload based on measured pulmonary artery pressure involves varying, for each repetition of an acute burst protocol, a parameter of pacing applied to a patient's heart during the acute burst protocol. Pulmonary artery pressure is measured during the repetitions of the acute burst protocol. The length of the repetitions is chosen so that the patient's baroreflex system does not adjust to the varied parameter of pacing during the repetitions of the acute burst protocol. An optimum ventricular preload is determined based on the measured pulmonary artery pressure. Pacing therapy is provided using a value of the parameter that is selected based on the determination of optimum ventricular preload.

15 Claims, 9 Drawing Sheets

U.S. PATENT DOCUMENTS

| | | |
|---|---|---|
| 6,440,066 B1 | 8/2002 | Bardy |
| 6,640,135 B1 | 10/2003 | Salo et al. |
| 6,748,271 B2 | 6/2004 | Spinelli et al. |
| 6,772,005 B2 | 8/2004 | Casavant et al. |
| 6,871,088 B2 | 3/2005 | Chinchoy |
| 6,985,772 B2 | 1/2006 | Holmstrom et al. |
| 7,027,866 B2 | 4/2006 | Warkentin |
| 7,107,093 B2 | 9/2006 | Burnes |
| 7,181,285 B2 | 2/2007 | Lindh |
| 7,215,998 B2 | 5/2007 | Wesselink et al. |
| 7,302,295 B2 | 11/2007 | Stahmann et al. |
| 7,343,199 B2 | 3/2008 | Hatlestad et al. |
| 2003/0040777 A1 | 2/2003 | Shemer et al. |
| 2005/0027322 A1 | 2/2005 | Warkentin |
| 2005/0027323 A1* | 2/2005 | Mulligan et al. ............... 607/18 |
| 2005/0038479 A1 | 2/2005 | Deno et al. |
| 2005/0109338 A1 | 5/2005 | Stahmann |
| 2005/0234517 A1 | 10/2005 | Braunschweig et al. |
| 2006/0173493 A1 | 8/2006 | Armstrong et al. |
| 2006/0247702 A1* | 11/2006 | Stegemann et al. ............ 607/17 |
| 2007/0060959 A1* | 3/2007 | Salo et al. ...................... 607/6 |
| 2007/0293897 A1 | 12/2007 | Sheldon et al. |

OTHER PUBLICATIONS

Ogoh et al.., "Cardiopulmonary Baroreflex is Reset During Dynamic Exercise", J. Appl Physiol, 100, 2006, pp. 51-59.

Nakamoto et al.., "Beat-to-Beat Modulation of Atrioventricular Conduction during Dynamic Exercise in Humans", Japanese Journal of Physiology, vol. 55, 2005, pp. 37-51.

U.S. Office Action dated Apr. 27, 2009 from U.S. Appl. No. 11/799,794, 6 pages.

U.S. Office Action dated Aug. 6, 2009 from U.S. Appl. No. 11/799,794, 23 pages.

U.S. Office Action dated Apr. 27, 2009 from U.S. Appl. No. 11/799,794, 24 pages.

U.S. Office Action Response dated Jun. 29, 2009 from U.S. Appl. No. 11/799,794, 6 pages.

U.S. Office Action Response dated Nov. 5, 2009 from U.S. Appl. No. 11/799,794, 11 pages.

U.S. Office Action Response dated Feb. 10, 2010 from U.S. Appl. No. 11/799,794, 11 pages.

Office Action dated Feb. 24, 2010 for U.S. Appl. No. 11/799,794, 16 pages.

Office Action Response dated May 14, 2010 from U.S. Appl. No. 11/799,794, 10 pages.

Office Action dated Jun. 16, 2010 from U.S. Appl. No. 11/799,794, 15 pages.

Office Action dated Jun. 8, 2010 from U.S. Appl. No. 11/894,081, 8 pages.

International Search Report and Written Opinion dated Nov. 17, 2008 from PCT Application No. PCT/US2008/009612, 15 pages.

International Preliminary Report on Patentability dated Mar. 4, 2010 from PCT Application No. PCT/US2008/009612, 10 pages.

Examiner Interview Summary dated Aug. 18, 2010 from U.S. Appl. No. 11/799,794, 4 pages.

Office Action dated Aug. 26, 2010 from U.S. Appl. No. 11/799,794, 12 pages.

Office Action Response dated Oct. 26, 2010 from U.S. Appl. No. 11/799,794, 9 pages.

Examiner Interview Summary dated Oct. 27, 2010 from U.S. Appl. No. 11/799,794, 3 pages.

Advisory Action dated Nov. 15, 2010 from U.S. Appl. No. 11/799,794, 3 pages.

Office Action Response dated Nov. 26, 2010 from U.S. Appl. No. 11/799,794, 9 pages.

File History for U.S. Appl. No. 11/894,081 as retrieved from U.S. Patent and Trademark Office PAIR system on Nov. 23, 2010, 438 pages.

Office Action dated Jan. 24, 2011 from Australian Application No. 2008289617, 5 pages.

* cited by examiner

METHOD, APPARATUS, AND SYSTEM TO OPTIMIZE CARDIAC PRELOAD BASED ON MEASURED PULMONARY ARTERY PRESSURE

FIELD OF THE INVENTION

The present invention relates generally to cardiac pacing therapy, and more specifically, to optimizing cardiac preload based on measured pulmonary artery pressure.

BACKGROUND OF THE INVENTION

Cardiac rhythm management devices have been developed that provide pacing stimulation to one or more heart chambers in an attempt to improve the rhythm and coordination of atrial and/or ventricular contractions. Cardiac rhythm management devices typically include circuitry to sense signals from the heart and a pulse generator for providing electrical stimulation to the heart. Leads extending into the patient's heart chamber and/or into veins of the heart are coupled to electrodes that sense the heart's electrical signals and for delivering stimulation to the heart in accordance with various therapies for treating cardiac arrhythmias.

Pacemakers are cardiac rhythm management devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

Pacing therapy has been used in the treatment of various types of heart failure (HF). Generally, HF is associated with diminished pumping power of the heart, resulting in the inability to deliver enough blood to meet the demands of peripheral tissues. HF may cause weakness, loss of breath, and build up of fluids in the lungs and other body tissues. HF may affect the left heart, right heart or both sides of the heart. For example, HF may occur when deterioration of the muscles of the heart produce an enlargement of the heart and/or reduced contractility. The reduced contractility decreases the cardiac output of blood and may result in an increased heart rate. In some cases, HF is caused by unsynchronized contractions of the left and right heart chambers, such as atrial or ventricular dysynchrony. When the left or right ventricles are affected, unsynchronized contractions can significantly decrease the pumping efficiency of the heart.

Pacing therapy can promote synchronization of heart chamber contractions to improve cardiac function. This is generally referred to as cardiac resynchronization therapy (CRT). Some cardiac pacemakers are capable of delivering CRT by pacing multiple heart chambers. Pacing pulses are delivered to the heart chambers in a sequence that causes the heart chambers to contract in synchrony, increasing the pumping power of the heart and delivering more blood to the peripheral tissues of the body. In the case of dysynchrony of right and left ventricular contractions, a biventricular pacing therapy may pace one or both ventricles. Bi-atrial pacing or pacing of all four heart chambers may alternatively be used.

Pacing therapy has been proven valuable in halting physiological effects associated with decreased cardiac function. In some cases, pacing therapy has been shown to provide of a temporary or a permanent correction of physical deterioration of the heart resulting from the heart disease, a process known as reverse remodeling. Identification and application of pacing therapies that contribute to reverse remodeling can therefore be valuable in extending the lives of patients who have experienced some forms of heart failure.

SUMMARY OF THE INVENTION

The present invention is directed to systems and methods for optimizing cardiac preload based on measured pulmonary artery pressure. A method according to an embodiment of the present invention involves varying, for each repetition of an acute burst protocol, a parameter of pacing applied to a patient's heart during the acute burst protocol. Pulmonary artery pressure is measured during the repetitions of the acute burst protocol. An optimum ventricular preload is determined based on the measured pulmonary artery pressure. Pacing therapy is provided using a value of the parameter that is selected based on the determination of optimum ventricular preload. In one embodiment, a method involves varying, for each repetition of an acute burst protocol, a parameter of pacing applied to a patient's heart during the acute burst protocol. Pulmonary artery pressure is measured during the repetitions of the acute burst protocol, and an optimum ventricular preload is determined based on the measured pulmonary artery pressure. Pacing therapy is provided using a value of the parameter that is selected based on the determination of optimum ventricular preload.

In more particular embodiments, the parameter of pacing may include any combination of a pacing delay, an atrioventricular pacing delay, a biventricular delay, an interatrial delay, and a pacing site of an implantable cardiac lead in the patient's heart. The method may also involve choosing a length of the repetitions of the acute burst protocol such that the patient's baroreflex system does not adjust to the varied parameter of pacing during the repetitions of the acute burst protocol.

In other, more particular embodiments, the method further involves measuring the pulmonary artery pressure between repetitions of the acute burst protocol to determine a baseline pulmonary artery pressure. In such a case, determining the optimum ventricular preload involves comparing the baseline pulmonary artery pressure with the pulmonary artery pressure measured during the repetitions of the acute burst protocol. In other arrangements, measuring pulmonary artery pressure during the repetitions of the acute burst protocol involves measuring pulmonary artery diastolic pressure. In such a case, determining the optimum ventricular preload based on the measured pulmonary artery diastolic pressure may involve determining the optimum ventricular preload based on a maximum value of the pulmonary artery diastolic pressure.

In other, more particular embodiments of the method, determining the optimum ventricular preload based on the measured pulmonary artery pressure involves determining the optimum ventricular preload based on a maximum value of the pulmonary artery pressure. In one variation, providing the pacing therapy involves performing ambulatory optimization of a pacing interval applied to the patient's heart. In another variation, the method further involves varying patient posture during selected ones of the repetitions of the acute burst protocols.

In another embodiment of the invention, a medical system includes one or more electrodes for delivering pacing pulses to a patient's heart. An energy delivery and sensing unit is coupled to the one or more electrodes. The system also includes a pulmonary artery pressure sensor capable of making pulmonary artery pressure measurements and a memory configured to store at least the pulmonary artery pressure measurements. A controller is coupled to the memory, pulmonary artery pressure sensor, and the energy delivery and sensing unit. The controller is configured to vary, for each repetition of an acute burst protocol, a parameter of pacing applied to the patient's heart via the energy delivery and sensing unit during the acute burst protocol. The controller stores the pulmonary artery pressure measurements made during the repetitions of the acute burst protocol, and provides pacing therapy using a value of the parameter that is selected based on an optimum ventricular preload that is determined via the stored pulmonary artery pressure measurements.

In more particular embodiments of the system, the parameter of the pacing may include any combination of a pacing delay and a pacing site of the electrodes. In one configuration, the controller is further configured to store the pulmonary artery pressure measurements between repetitions of the acute burst protocol to determine a baseline pulmonary artery pressure. In such a case, the optimum ventricular preload is determined by comparing the baseline pulmonary artery pressure with the pulmonary artery pressure measurements stored during the repetitions of the acute burst protocol.

In more particular embodiments of the system, the pulmonary artery pressure measurements include pulmonary artery diastolic pressure measurements. In other arrangements, the controller is further configured to determine the optimum ventricular preload based on a maximum pressure measurement made during the repetitions of the acute burst protocol. The controller may also be further configured to provide the pacing therapy during ambulatory optimization of a pacing interval applied to the patient's heart.

In another embodiment of the invention, a medical system includes means for applying pacing to a patient's heart for multiple repetitions of an acute burst protocol. A parameter of the pacing is varied for each repetition of the acute burst protocol. The system also includes: means for measuring pulmonary artery pressure during the repetitions of the acute burst protocol; means for determining an optimum ventricular preload based on the measured pulmonary artery pressure; and means for providing pacing therapy using a value of the parameter of pacing that is selected based on the determination of optimum ventricular preload. The system may optionally include means for measuring the pulmonary artery pressure between repetitions of the acute burst protocol to determine a baseline pulmonary artery pressure. In such a case, the means for determining the optimum ventricular preload further includes means for comparing the baseline pulmonary artery pressure with the pulmonary artery pressure measured during the repetitions of the acute burst protocol.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
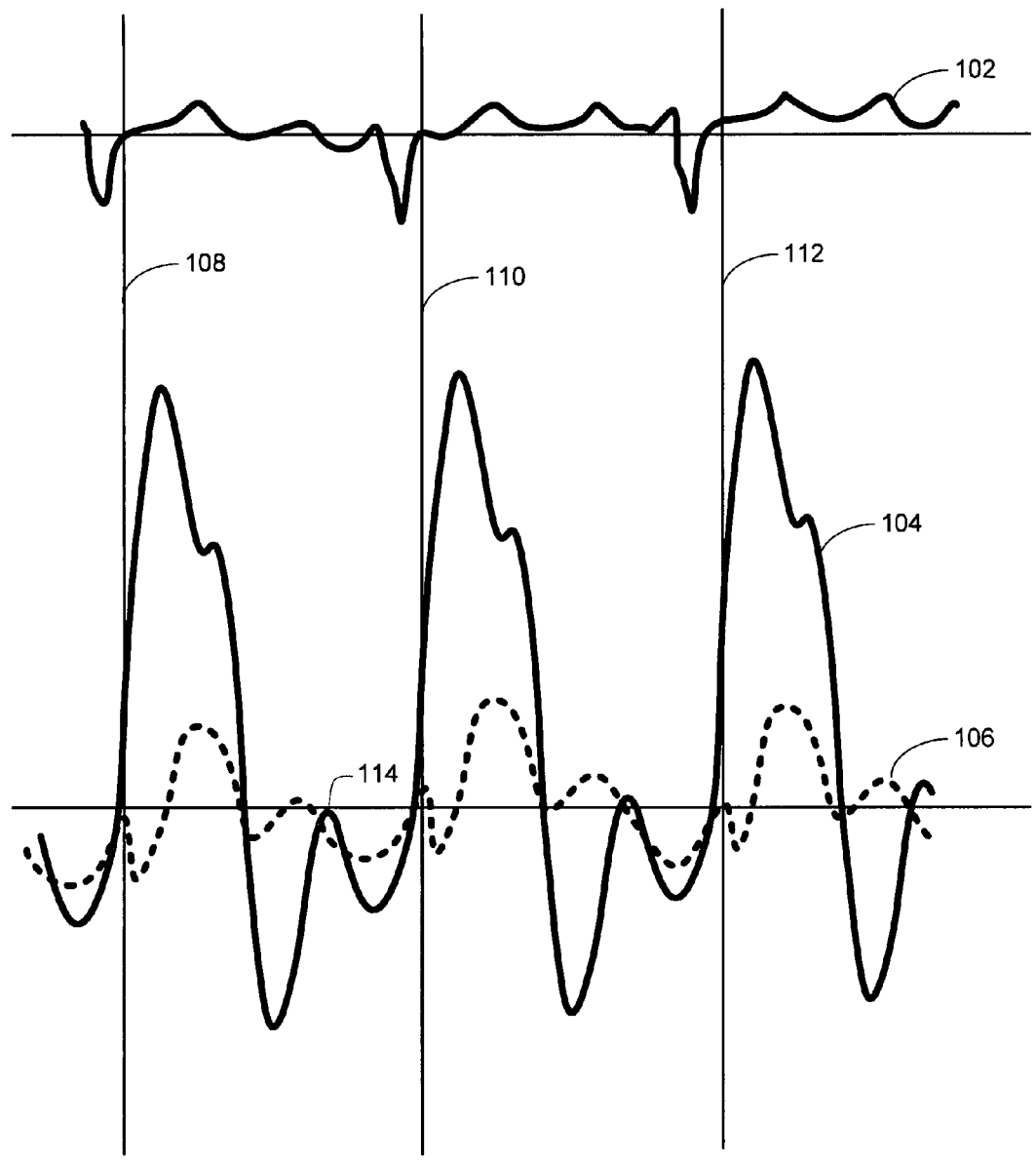
FIG. 1 shows various waveforms depictive of a cardiac cycle, from which timing intervals may be measured and used for optimizing cardiac preload in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described hereinbelow. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

Embodiments of the invention are directed to systems and methods for optimizing left ventricular (LV) preload using pacing therapies. Embodiments of the invention are directed to making direct measurements of pulmonary pressure during an acute burst protocol and determining an optimum ventricular preload based on these pressure measurements. This optimization of preload may be implemented as part of an implantation procedure and/or be implemented as part of ambulatory CRT. For example, when the activity of a patient is increasing, it may be desired to acutely increase LV preload.

Patients with implanted cardiac rhythm management devices sometimes suffer from heart conditions such as congestive heart failure (CHF). CHF is a condition in which the heart's ability to efficiently pump blood is substantially reduced. In some cases, CHF is caused by the wall muscles of the right and/or left sides of the heart being weaker than usual due to genetic causes. In other cases, the wall muscles are weakened due to being stretched abnormally during heart filling/contraction because of conditions such as arterial plaque, stress, smoking, etc. If the heart muscles of the left side of the heart deteriorate, the left atrium and/or left ventricle become enlarged. This condition is referred to as left ventricular systolic dysfunction (LVSD).

Patients with LVSD may experience decreased hemodynamic performance of the left ventricle over time. To compensate, the heart rate becomes increased, as resting time between contractions may decrease. In addition, the enlargement of the heart tissue due to LVSD may cause ventricular depolarization signals to travel more slowly through the left side of the heart in the right ventricle. This causes the left ventricle to contract somewhat later than the right ventricle, and further reduces the hemodynamic efficiency of the heart.

Pacing therapies that coordinate atrial and/or ventricular contractions may be used to increase the cardiac efficiency of LVSD patients. Depending on the patient, pacing therapies may be applied via one or more electrodes that are positioned in one or more heart chambers. Multiple chamber pacing therapies may include any combination of pacing the left and right ventricles (biventricular), pacing a ventricle and an atrium (atrioventricular), and pacing the left and right atriums (interatrial). These pacing therapies may also utilize sensors to detect depolarizations the electrode sites, and adjust pacing appropriately.

Multi-chamber pacing therapies such as CRT can improve the hemodynamic performance of the left ventricle by reducing dyssynchrony. In particular, CRT in the form of biventricular pacing has been shown to improve hemodynamic status acutely, as well as reducing heart failure symptoms and improving systolic function. Biventricular pacing has also been shown to cause reverse remodeling, which refers to an improvement left ventricular pumping efficiency due to a reduction in some deteriorations of heart physiology.

One pacing strategy used to increase cardiac output is to optimize AV delay such as to maximize the contractility (LVdp/dt) of the left ventricle. This contractility is maximized when the left ventricle experiences the maximum end diastolic volume, or preload. This is known as the Frank Starling mechanism. The maximum left ventricular end diastolic volume (LVEDV) can be directly correlated to left ventricular end diastolic pressure (LVEDP). Therefore, pacing therapies that can be shown to maximize LVEDP also increase cardiac output of the left ventricle (LVEDV), thus increasing dp/dt, stroke volume, and preload.

In some cases, it may be difficult to measure LVEDP directly. A more common approach is to indirectly measure LVEDP. It has been found that pulmonary artery diastolic pressure (PAD) may be used to estimate LVEDP. In reference now to FIGS. 1 and 2, correlations between PAD and LVEDP/LVEDV are shown that may be applied to methods, systems, and apparatus according to embodiments of the invention. In FIG. 1, there is shown various waveforms depictive of cardiac cycles, in particular waveforms developed from electrocardiogram (ECG), PAD, and left ventricular pressure (LVP) measurements. It is understood that measurements useful for implementing embodiments of the present invention may be developed using a wide variety of sensors, waveforms, waveform features, and combinations of sensors, waveforms and waveform features, and that those associated with FIG. 1 and other figures are provided for non-limiting illustrative purposes only, and should not be construed as limiting the scope of the present invention.

The waveforms shown in FIG. 1 are generally depictive of approximately three cardiac cycles, as best seen in the ECG waveform 102. Waveform 104 represents pulmonary artery pressure and waveform 106 represents left ventricular pressure. The indicators 108, 110, and 112 indicate points of LVEDP on the left ventricular waveform 106 for each of the three cardiac cycles. The LVEDP 108, 110, 112 is phase shifted from the PAD (e.g., point 114), and there is a correlation between magnitudes of LVEDP and PAD, as seen in the plot of FIG. 2.

Figure 2:
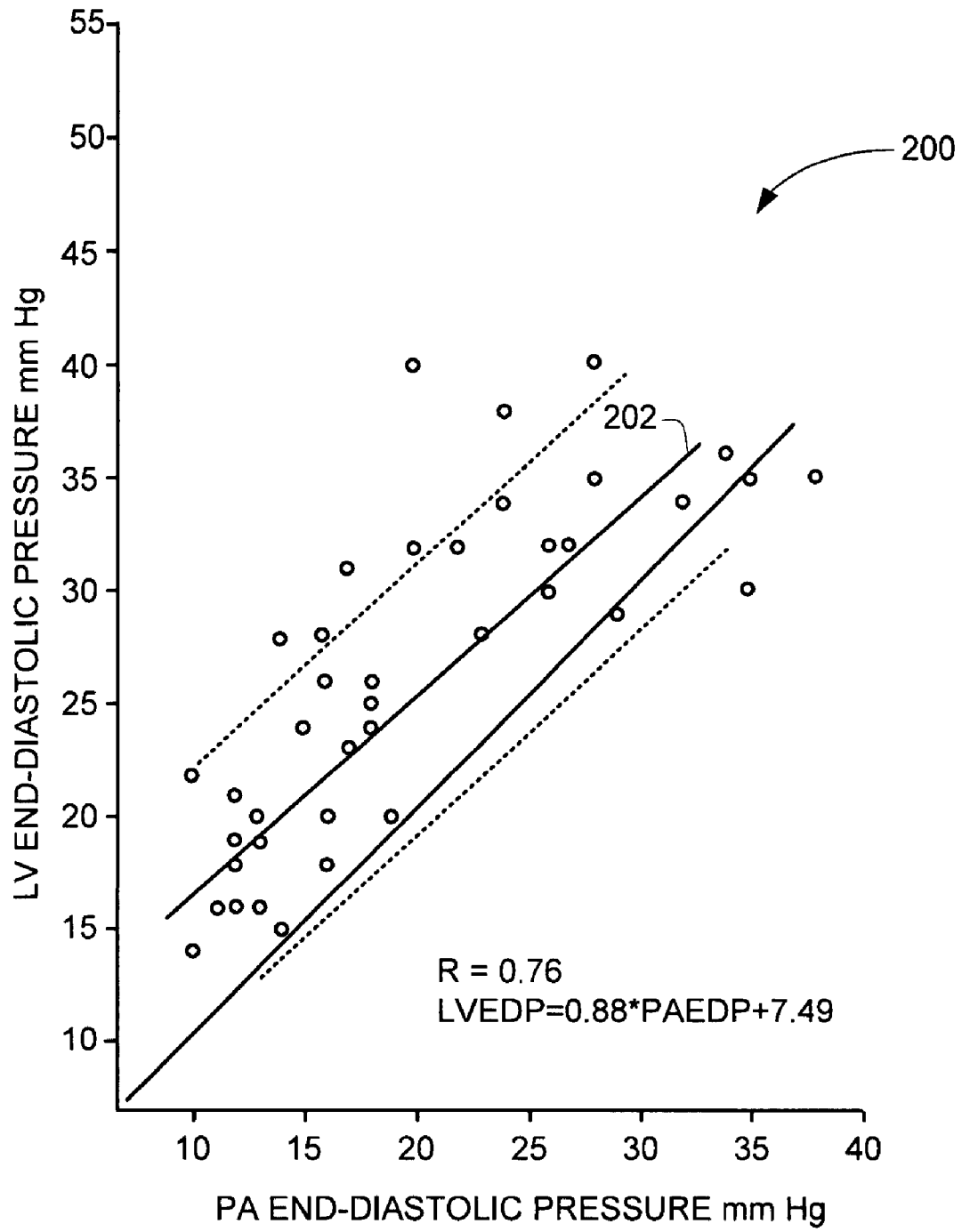
FIG. 2 is a plot of data illustrating a correlation between left-ventricular end-diastolic pressure and pulmonary artery end-diastolic pressure in accordance with embodiments of the present invention.

The plot 200 of data shown in FIG. 2 was acquired for a population of CRT patients and is useful for showing the correlation between pulmonary artery end diastolic pressure (PAEDP) and LVEDP. The population for analyzing the correlation preferably includes patients with similar left ventricular dysfunctions. As can be seen from the results of this population, a linear relation between LVEDP and PAEDP (shown as line 202) can be expressed as:

$$LVEDP=0.88*PAEDP+7.49 \qquad [1]$$

It will be appreciated that the equation [1] is merely an exemplary result that indicates a linear correlation between LVEDP and PAEDP, and is not necessarily needed or used to estimate actual LVEDP in embodiments of the invention. Generally, methods and apparatus described herein can use PAEDP as a proxy for LVEDP measurements, such as determining whether the LVEDP pressure is increasing or decreasing from a baseline value. Correlations between PAEDP and LVEDP can be utilized by apparatus that can make direct pulmonary artery pressure measurements. As will be described in greater detail hereinbelow, an implantable pacing system may include a pressure sensor capable of making direct pulmonary artery pressure measurements.

A system according to embodiments of the invention can use pulmonary pressure measurements for, among other things, improving hemodynamic heart performance by maximizing LV preload on an acute basis. Although PAEDP is one example of pulmonary artery pressure that may be optimized in order to optimize LVEDP/LVEDV, other pulmonary pressure measurements may be used for this purpose, such as pulmonary artery pulse pressure, pulmonary artery systolic pressure. These methods for optimizing LV preload are also applicable to systems that are capable of making direct measurements of LVP. Similarly, other physical measurements that have a strong correlation to LVEDP/LVEDV may be used in systems according to an embodiment of the invention.

Commonly, HF patients have high blood pressure, either as a cause or effect of heart conditions. As such, treating those HF patients involves lowering blood pressure over the long term. However, by acutely maximizing LVEDP (e.g., doing so over a short period of time), the cardiac output can be momentarily and periodically increased to improve heart condition (e.g., induce reverse remodeling). Generally, acute therapies rely on the heart's short-term reaction to some variation of a therapy parameter before the body's baroreflexes can adjust to the variation.

Figure 3:
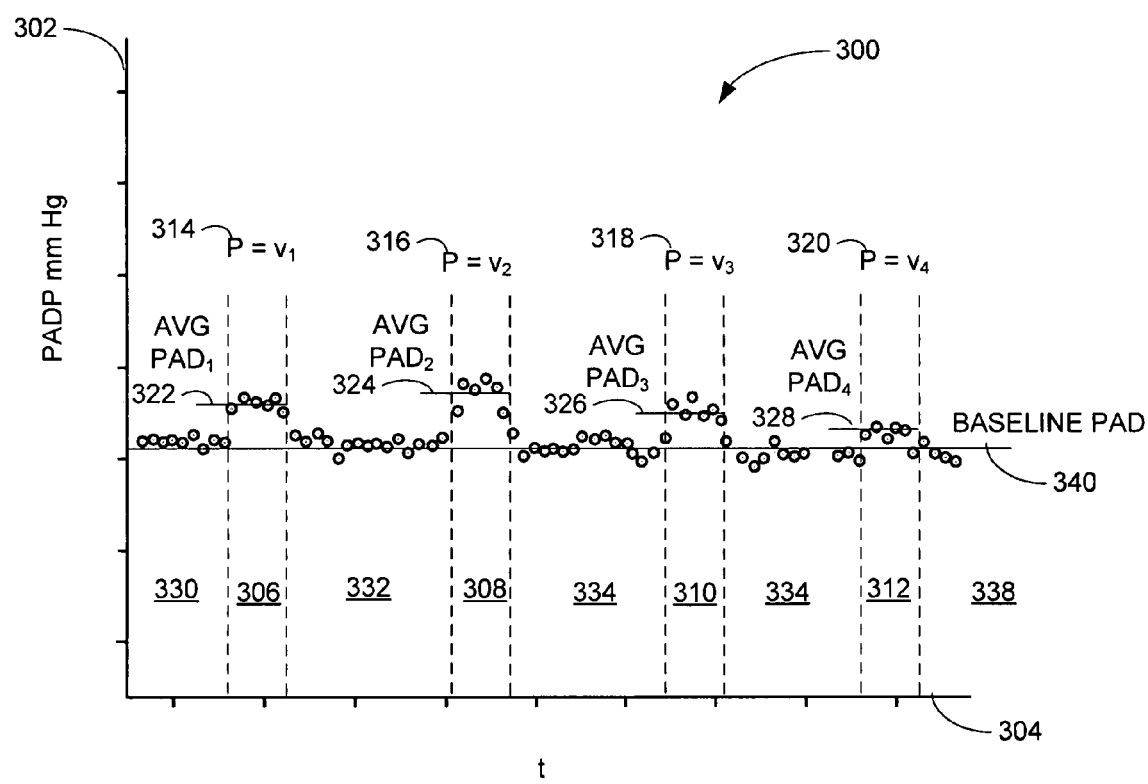
FIG. 3 is a plot that illustrates varying pacing parameters in an acute burst protocol according to an embodiment of the invention.

According to embodiments of the invention, a parameter of pacing applied to a patient's heart is varied during multiple repetitions of an acute burst protocol. The parameter is different for each of the bursts, and the resulting changes to pulmonary pressure (or other measurement correlated to LVEDP/LVEDV) are observed. Pulmonary pressures that occur in time periods between the bursts may also be observed in order to determine a baseline reading. Assuming that one of the variations results in an optimal pulmonary pressure reading, the value of that variation may be used as part of an acute therapy for increasing cardiac output. Determining optimum readings from an acute burst therapy may also have other applications, such as determining optimal placement of pacing leads. The plot 300 of FIG. 3 shows an example of how pacing parameters may be varied to determine optimum ventricular preload according to an embodiment of the invention.

The plot 300 includes a vertical axis 302 that indicates PAD pressure (alternatively referred to herein as PAD or PADP), and in particular PAEDP. However, it will be appreciated that other pulmonary pressures (or other physiological measurements) may be utilized that are found to strongly correlate to LVEDP. For example, a combination of PAEDP with another pulmonary pressure made during the cardiac cycle may provide improved estimation accuracy of LVEDP over those made using PAEDP alone. The horizontal axis 304 indicates time, and the variation of PAD 302 over time 304 is used to assist optimizing cardiac flow by increasing LV preload.

As seen in the plot 300, four burst intervals 306, 308, 310, and 312 are demarcated. The selection of four intervals 306, 308, 310, 312 is arbitrary and made for purposes of illustration. Generally, safety considerations and the accuracy of measurements will dictate a reasonable number of intervals. As a result, the determination of the number and composition of the intervals are typically made on a case-by-case basis by the clinician.

During each of these intervals 306, 308, 310, 312, a parameter (P) of pacing is changed. This parameter may include a delay (e.g., AV delay, VV delay) applied to implantable pacing electrodes, or any other timing or electrical characteristic applied to such electrodes. Other parameters that may be varied include the location of the pacing electrodes. The location may be varied for purposes of characterization by physically moving the electrode (e.g., during implantation procedures). In an ambulatory, closed loop application, it is more typical that the location may be changed by choosing particular electrodes of a multi-electrode lead.

As seen in FIG. 3, the parameter P is set to four different values 314, 316, 318, 320 for each of the respective burst intervals 306, 308, 310, 312. As a result, the measured PADP may take on a different value during the intervals 306, 308, 310, and 312, as represented by the average values 322, 324, 326, and 328, respectively. After the burst protocols are complete, one of the average burst protocol values 322, 324, 326, and 328 may be determined to be optimal. In many cases, the optimal value of the averages 322, 324, 326, and 328 may be that value that has the maximum value, here represented by value 324 at P=$v_2$. This value 324 corresponds to the highest acute level of PADP 302 measured during the therapy.

Not only are the values 314, 316, 318, 320 different from each other, but they may be different from pacing parameters used (if any) during time periods between the burst intervals 306, 308, 310, 312. These time intervals, represented as sensing intervals 330, 332, 334, 336, 338 allow for the heart to return to a normative state before, between, and after applications of the burst intervals 306, 308, 310, 312. The measurements made during the sensing intervals 330, 332, 334, 336, 338 can be used to determine a baseline value 340 of PADP. In many situations, there may be no pacing therapy applied during the rest intervals 330, 332, 334, 336, 338, and therefore the baseline 340 may represent a non-paced value of PADP. In other cases, an established value of the pacing parameter may be applied during the rest intervals 330, 332, 334, 336, 338. In this latter case, the values 322, 324, 326, 328 represent a change in PADP due to a change in the varied parameter, P from the baseline pacing levels.

As previously described, a number of different pacing parameters may be changed during acute burst therapy according to embodiments of the invention, including inter-chamber pace timing and lead location. The phase where those parameters that result in maximum ventricular preload may be referred to herein as "characterization." Characterization may be performed in a clinical setting, where a patient's condition is actively monitored by a clinician. However, it may be possible to include some type of ambulatory characterization, where various (typically mild) variations of a parameter are changed in use and under a number of different patient conditions (e.g., sleep, exercise, working) to either determined new parameter values or to optimize existing parameters. Any optimum parameters found during characterization can be used in a regular regime of therapy, typically by application via implantable pacing system.

Note that the change of variables 314, 316, 318, 320 between subsequent burst intervals 306, 308, 310, 312 is only one example of how characterization may be performed. In other examples, the variable P may be set to the same variable for multiple consecutive or non-consecutive bursts. Further, the characterization protocol may take into account various states of the patient, including posture (e.g., standing, sitting, prone), activity levels, drug therapies, and other conditions/states. The programmability of implanted and/or external pacing apparatus allows for a flexible tailoring of the characterization data in order to optimize preload under a variety of conditions.

Figure 4:
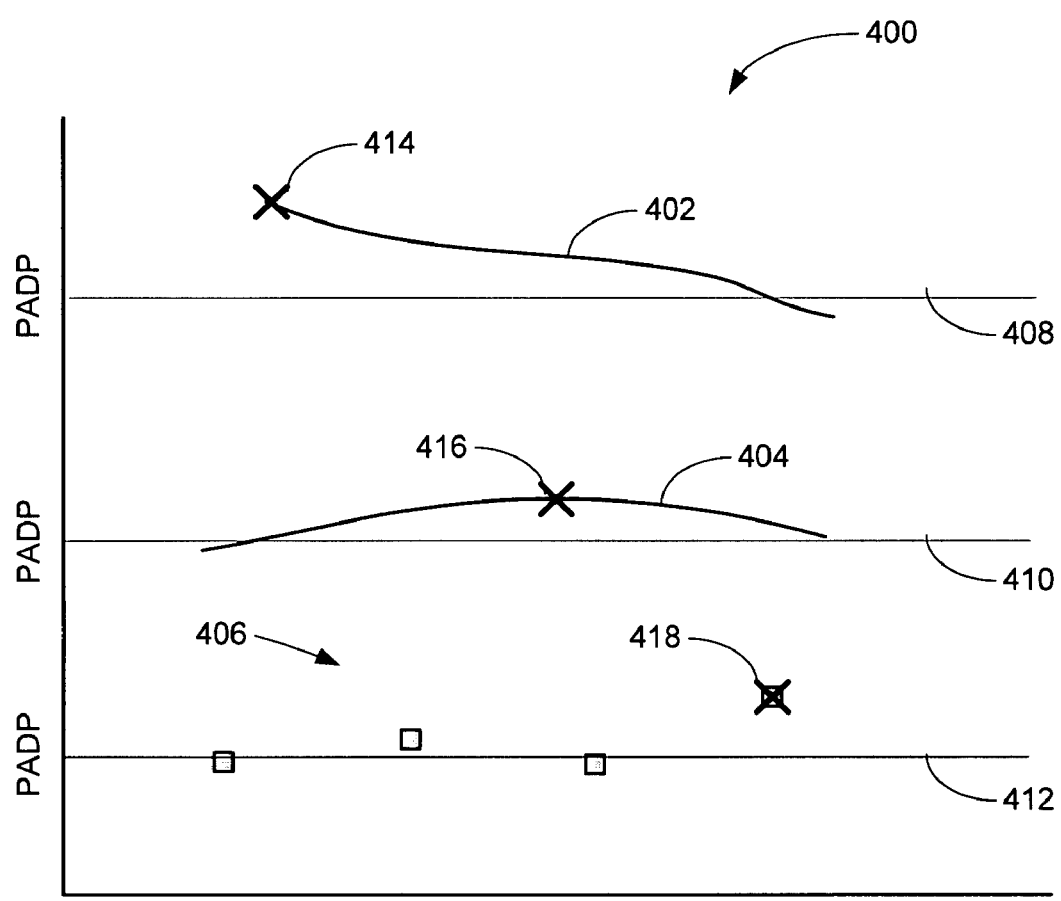
FIG. 4 is a plot illustrating the application of an acute burst protocol to different pacing parameters according to an embodiment of the invention.

As shown in FIG. 3, only a single parameter is changed while characterizing responses of a particular patient to that parameter. However, it is contemplated that the patient's response to multiple parameters may be determined by multiple characterization protocols such as shown in FIG. 3. In reference now to FIG. 4, a plot 400 illustrates an example of three characterization results 402, 404, 406 that may be observed for a particular patient. Each result may be obtained by changing a single pacing parameter in an acute burst protocol, and the parameter may be continuously or discretely variable. For example, the parameters associated with results 402 and 404 may be continuously variable (e.g., timing) and the parameter associated with results 406 may be discrete (e.g., location of activated electrode on multiple electrode lead).

Each result 402, 404, 406 is associated with a respective baseline value 408, 410, 412. For purposes of clarity, the baselines 408, 410, 412 and results 402, 404, 406 are plotted in separate vertical regions. However, under similar physiological conditions, it may be assumed that the baseline values 408, 410, 412 may be substantially similar. The results 402, 404, 406 may also be determined for multiple various patient conditions, such as rest/work states, postures, drug therapies, etc. In the illustrated example, results 402, 404, 406 have respective points of maximum PADP, 414, 416, and 418. The parameters associated with those maximum results 414, 416, 418 may be obtained directly from the results 402, 404, 406, or obtained by way of interpolation and/or extrapolation.

Generally, an ambulatory pacing optimization therapy can vary combinations of parameters based on the characterization results 402, 404, 406. For example, a treatment may vary both AV-delay and location in order to acutely increase LV preload. Such a combination of parameters may also be characterized together before being used for treatment. For example, an optimum value for each of the parameters may be selected from the results 402, 404, 406 and small variations may be introduced to ensure that the combination results in optimum preload. In another example, the optimization of both location and timings may be performed during implantation in order guide lead location, and thereafter timing changes (and/or electrode selection) may be applied as part of ambulatory therapy.

For example, consider the case where AV delay and location are varied as part of the acute therapy. Characterization shows that $AV_{opt}$ and $LOC_{opt}$ are the optimum values of AV delay and location found through single parameter characterization. AV− and AV+ may be small variations respectively less than and greater than $AV_{opt}$, and LOC+ and LOC− may be alternate locations that still showed increased PAD in an acute burst protocol, although not as much as $LOC_{opt}$. Therefore, another set of burst protocol characterization may use some or all of (AV−, LOC−), (AV−, LOC+), (AV+, LOC−) and (AV+, LOC+) to determine whether the combination of $AV_{opt}$ and $LOC_{opt}$ is optimal, and make adjustments if not.

Figure 5:
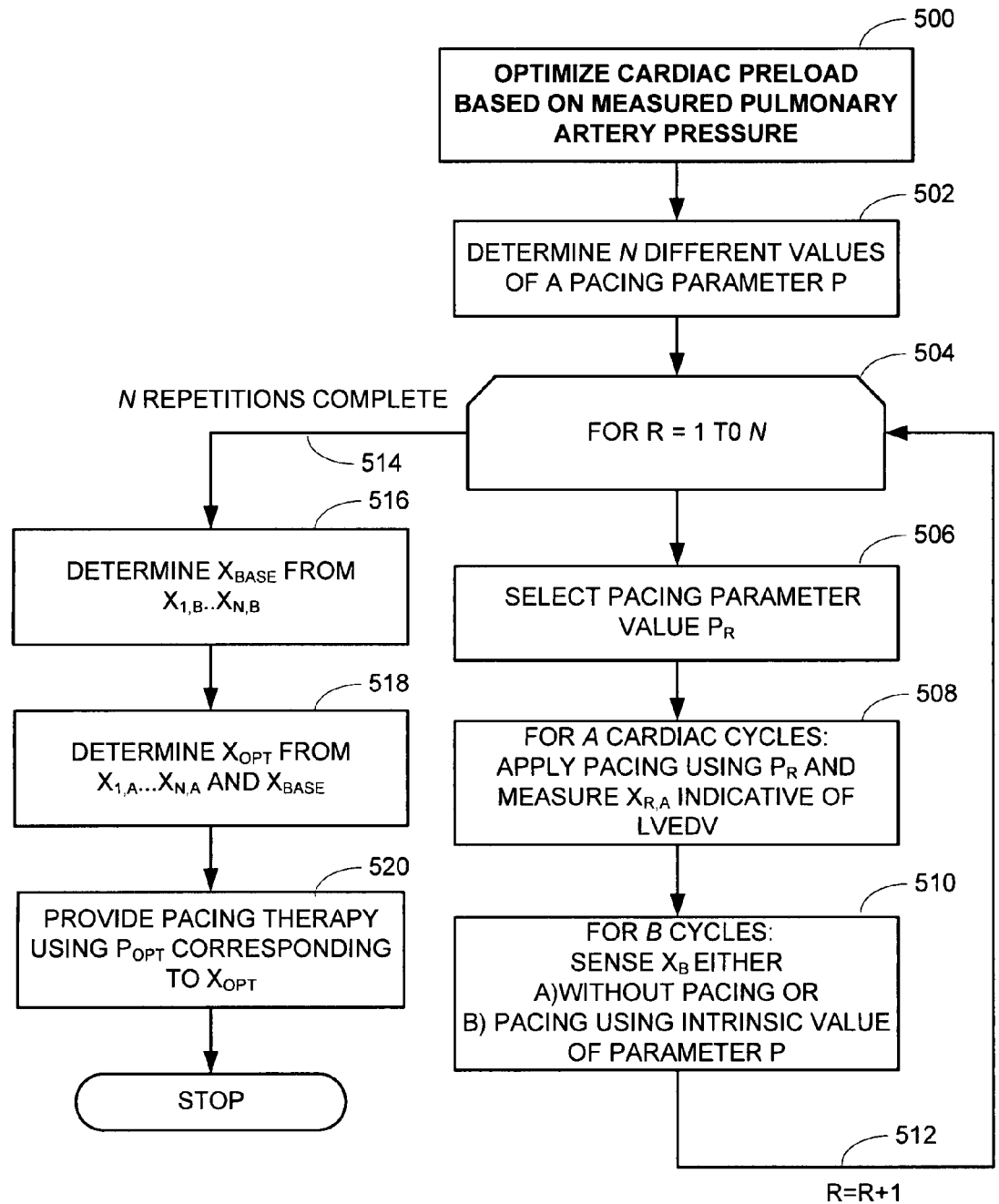
FIGS. 5-7 are flow charts that illustrate various processes associated with preload optimization methodologies in accordance with embodiments of the present invention.

Turning now to FIG. 5, there is shown a flow chart that illustrates a procedure 500 for optimizing cardiac preload based on measured pulmonary artery pressure according to an embodiment of the invention. The procedure involves determining 502 n-different values of a pacing parameter P. The parameter P may be any value that affects the application of electrical impulses to cardiac tissue. Typical examples of P include AV delay, VV delay, lead location, etc. The variable P may be continuous or discrete, and the acceptable range of P may be patient-specific.

The procedure 500 involves entering a loop 504 that is repeated n-times, once for each value of P. For each repetition R of the loop 504, one of the pacing values is selected 506, the selected value being annotated as $P_R$. The selected value of $P_R$ is used to apply pacing 508 for A-cardiac cycles, and a value $X_{R,A}$ is sensed during the A-cycles. The sensed value $X_{R,A}$ may be any value indicative of LVEDV and/or LVEDP. Typically, $X_{R,A}$ may be PAEDP and/or a direct measure of LVEDP. The number of repetitions, represented by A, is chosen to substantially affect LVEDP without the barometric function adjusting for the change in stroke volume. After the pacing 508 is applied, an intervening period of sensing 510 is performed for B-cardiac cycles. Typically, the value of B will be significantly larger than A.

The same value of X (e.g., PAEDP) that was sensed in the pacing phase 508 is at least sensed in the sensing phase 510 for the B-cycles. These latter measurements are represented as $X_B$. The sensing phase 510 may involve no pacing at all, or pacing using pre-established intrinsic values of a particular patient. After sensing 510, the value of R is incremented 512 and the loop 504 continues for another repetition.

After n-repetitions are complete 514, a baseline value of X ($X_{BASE}$) may be determined 516 using the measurements taken during one or all of the sensing periods 510. An optimal value (e.g., maximum PAD) of X ($X_{OPT}$) is determined 518 from the values sensed in pacing periods 508. The determination 518 of $X_{OPT}$ may also involve analyzing the baseline measured value $X_{BASE}$. Thereafter, a pacing therapy may be provided 520 using an actual or estimated optimal value of P ($P_{OPT}$) that is determined based on $X_{OPT}$.

Figure 6:
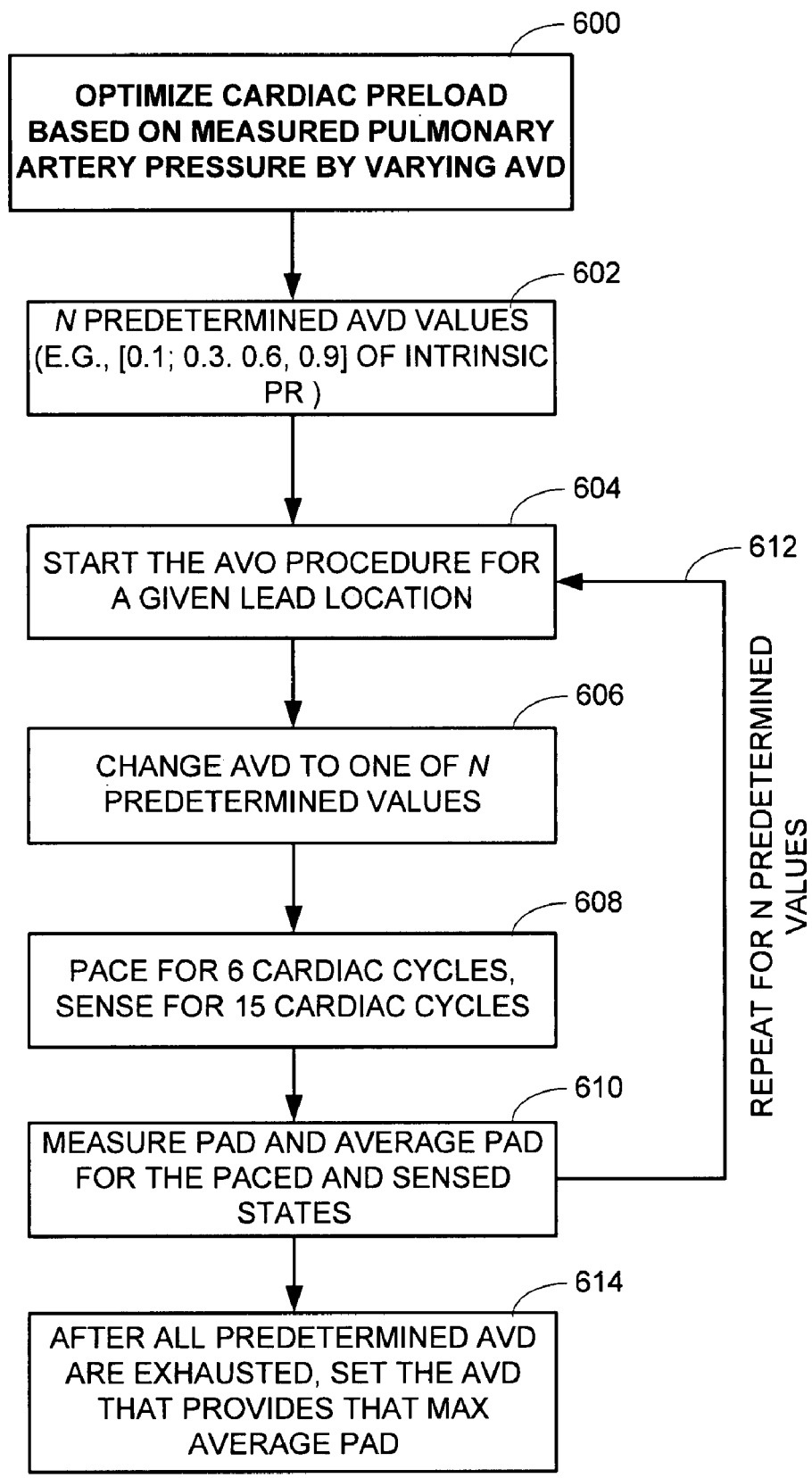

The procedure 500 may use any parameter P known in the art. One useful application involves using AV delay as the parameter P. In reference now to FIG. 6, there is shown a flow chart that illustrates a procedure 600 for optimizing cardiac preload based on measured pulmonary artery pressure by varying AV delay (AVD) according to an embodiment of the invention. The procedure 600 involves using n-predetermined AVD values. For example, the values may be 10%, 30%, 60% and 90% of a patient's intrinsic $P_R$ timing. An AV optimization (AVO) procedure is started 604 for a given lead location. The AVD is changed 606 to one of the n-predetermined AVD values, and a pacing/sensing series 608 is performed. In this example, the series 608 involves pacing for six cardiac cycles and sensing for 15 cardiac cycles. The series 608 may be repeated multiple times for the selected AV delay. The paced PAD and average (baseline) PAD is sensed 610 for the respective paced and sensed cycles. The subprocedure 604, 606, 608, 610 is repeated 612 for the n-predetermined AVD values. After all the predetermined AVD values are exhausted, the AVD is set 614 to the value the produced the maximum paced PAD.

Figure 7:
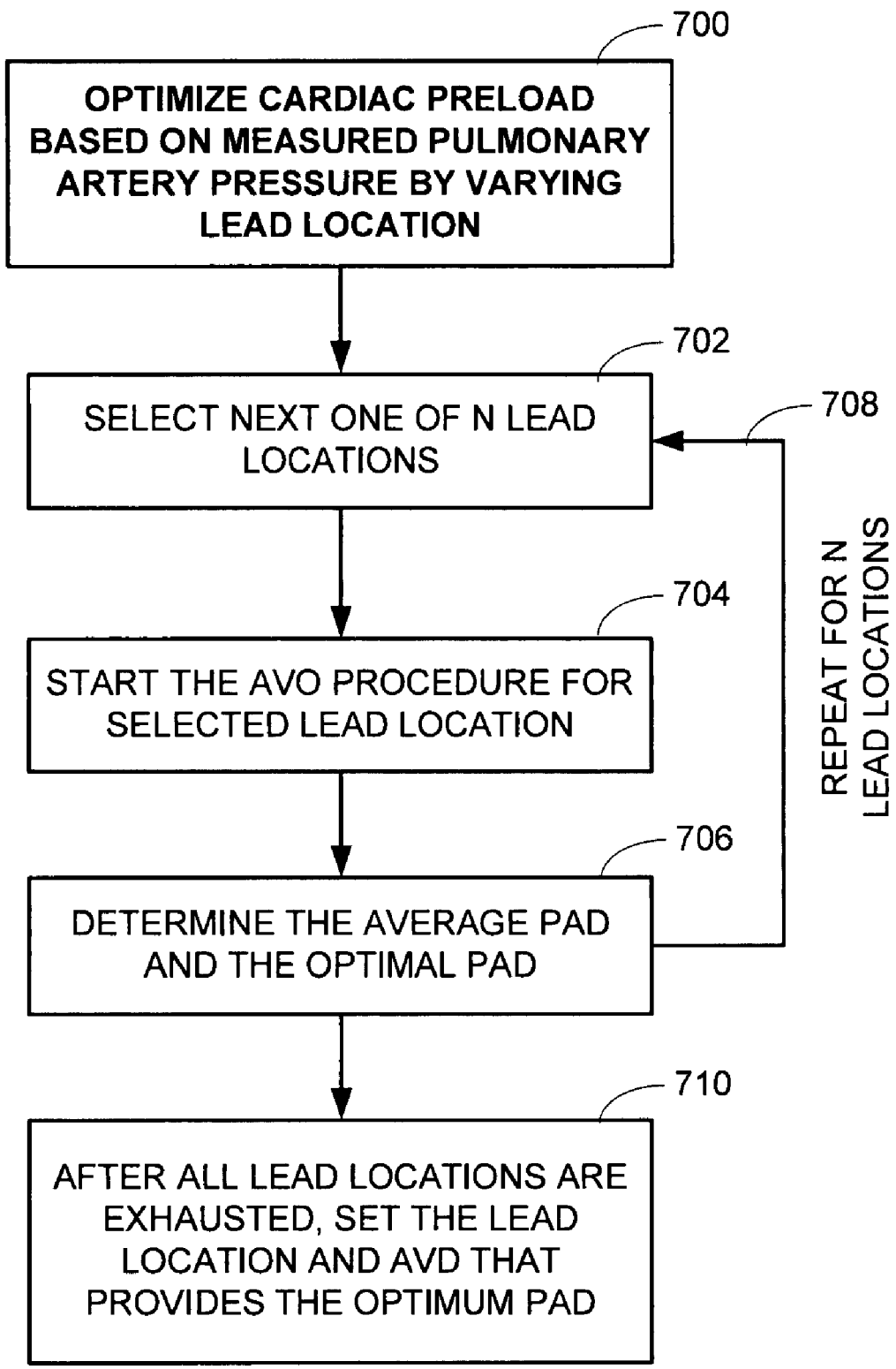

Turning now to FIG. 7, there is shown a flow chart that illustrates a procedure 700 for optimizing cardiac preload based on measured pulmonary artery pressure by varying lead location according to an embodiment of the invention. This procedure involves selecting 702 a next one of n-lead locations and starting an AVO procedure 704 for the selected location. For example, a procedure such as described in FIG. 6 may be used for the AVO procedure 704. As a result of the AVO procedure 704, an average and optimal PAD is determined 706, and the procedure is repeated 708 for the remaining locations. After all of the lead locations are exhausted, the lead location (and AVD) that result in the optimum (e.g., maximum) PAD are used 710 for therapy.

A pacing optimization methodology of the present invention may be implemented in a variety of medical diagnostic devices and systems, include implantable and patient-external devices and systems. For example, a pacing optimization methodology of the present invention may be implemented entirely by an implanted device (e.g., pacemaker, ICD, CRT devices), entirely by a patient-external system (other than cardiac electrodes/leads) or in a distributed manner by both implanted and patient-external devices or systems. In the context of a patient-external or distributed approach, various external systems may be employed, such as a programmer and/or a networked system, such as an advanced patient management system.

Figure 8:
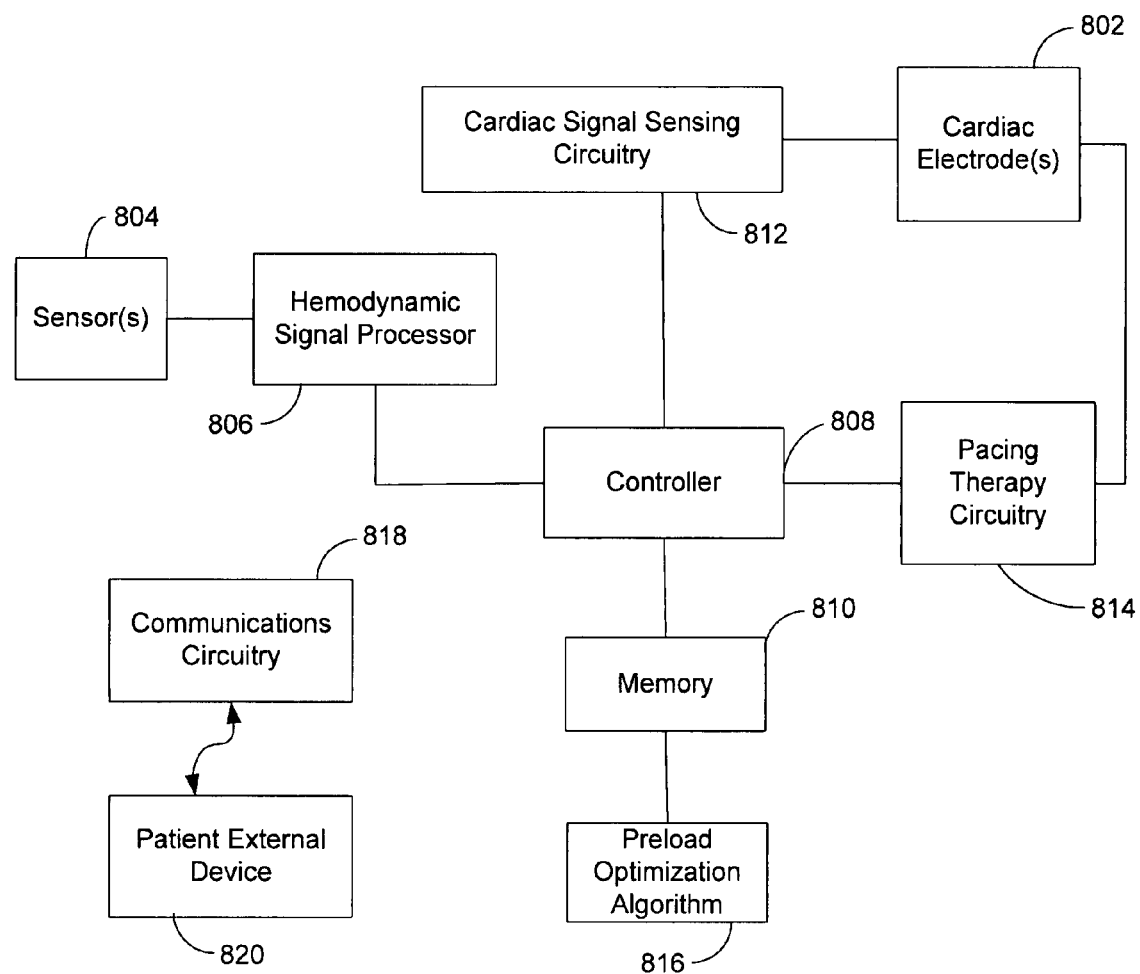
FIG. 8 is a block diagram of circuitry that may be used for implementing a preload optimization methodology in accordance with embodiments of the present invention.

In reference now to FIG. 8, a block diagram shows circuitry that implements a pacing optimization methodology in accordance with embodiments of the invention. One or more cardiac electrodes 802 may be positioned or disposed at multiple locations within a heart chamber or vasculature. In the context of an electrode implantation procedure, a candidate pacing site may be evaluated/optimized using a lead that includes one or more electrodes. In the context of post-implant evaluations, one or more implanted pacing sites may be evaluated/optimized.

One or more sensors 804 are configured to sense physiological factors indicative of a patient's hemodynamic status. Useful sensors 804 include a sensor or sensors that detect heart sounds (e.g., microphone, accelerometer), a pressure sensor (e.g., left arterial pressure sensor such as a pulmonary artery pressure sensor, left/right ventricular pressure sensor), and a cardiac stroke impedance sensor, among others. Signals produced by the one or more sensors 804 may be communicated to a hemodynamic signal processor 806, which processes the sensor signals for use by a controller 808.

The controller 808 is coupled to the hemodynamic signal processor 806, memory 810, cardiac signal sensing circuitry 812, and pacing therapy circuitry 814. The memory 810 is configured to store program instructions and/or data. In addition, the stored information may be used to provide a log of events for display or analysis at a later time. The memory 810 may be configured to store a preload optimization algorithm 816 a type described previously. Alternatively, the optimization algorithm 816 may be stored on a patient-external device or system. The controller 808 executes program instructions to implement a ventricular preload optimization procedure in accordance with embodiments of the present invention.

The controller 808 is preferably coupled to communications circuitry 818 which allows the device to communicate with other devices 820, such as a patient-external programmer or advanced patient management system. In some implementations, an advanced patient management (APM) system may be used to collect CRT patient data for purposes of developing patient population data from which a preload optimization algorithm may be trained. This data may be acquired from numerous CRT patients. The APM system or programmer may also be used to implement or facilitate implementation of the pacing site evaluation methodology of the present invention, particularly in the context of an electrode implantation procedure.

Figure 9:
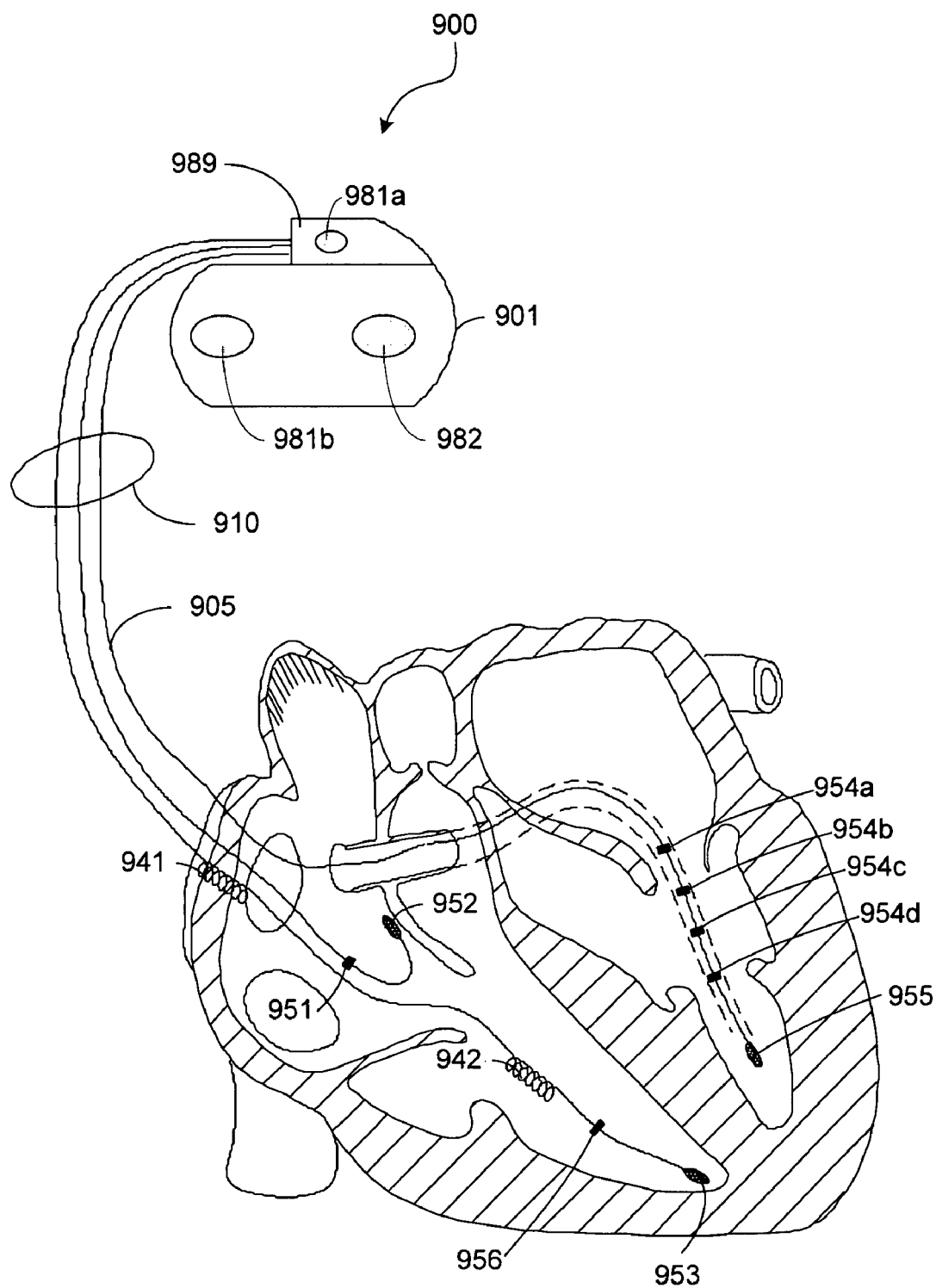
FIG. 9 illustrates a patient-implantable device that may be used in conjunction with a preload optimization methodology in accordance with embodiments of the present invention.

In reference now to FIG. 9, an embodiment of the present invention is shown implemented through the use of an implanted cardiac therapy device 900. The therapy device 900 includes cardiac rhythm management circuitry enclosed within an implantable housing 901. The CRM circuitry is electrically coupled to an intracardiac lead system 910. Portions of the intracardiac lead system 910 are shown inserted into the patient's heart. The lead system 910 includes cardiac pace/sense electrodes 951-956 positioned in, on, or about one or more heart chambers for sensing electrical signals from the patient's heart and/or delivering pacing pulses to the heart. The intracardiac sense/pace electrodes 951-956 may be used to sense and/or pace one or more chambers of the heart, including the left ventricle, the right ventricle, the left atrium and/or the right atrium. The lead system 910 may include one or more defibrillation electrodes 941, 942 for delivering defibrillation/cardioversion shocks to the heart.

The left ventricular lead 905 incorporates multiple electrodes 954a-954d positioned at various locations within, on or about the left ventricle. Stimulating the ventricle at multiple locations or at a single selected location may provide for increased cardiac output in a patients suffering from HF. In accordance with various embodiments described herein, one or more of the electrodes 954a-954d are selected for pacing the left ventricle. In other embodiments, leads having multiple pacing electrodes positioned at multiple locations within a chamber, such as the one illustrated by the left ventricular lead 905 of FIG. 10, may be implanted within any or all of the heart chambers. A set of electrodes positioned within one or more chambers may be selected. Electrical stimulation pulses may be delivered to the chambers via the selected electrodes according to a timing sequence and output configuration that enhances cardiac function.

Portions of the housing 901 of the implantable device 900 may optionally serve as one or multiple can or indifferent electrodes. The housing 901 is illustrated as incorporating a header 989 that may be configured to facilitate removable attachment between one or more leads and the housing 901. The housing 901 of the therapy device 900 may include one or more can electrodes 981b. The header 989 of the therapy device 900 may include one or more indifferent electrodes 981a.

The housing 901 and/or header 989 may include one or more hemodynamic sensors 982, such as an accelerometer or microphone. One or more cardiac leads 910 or separate sensor leads may incorporate one or more hemodynamic sensors, such as a pulmonary arterial pressure sensor. The cardiac electrodes and/or other sensors disposed within or on the housing 901 or lead system 910 of the therapy device 900 may produce signals used for detection and/or measurement of various physiological parameters, such as transthoracic impedance, respiration rate, minute ventilation, heart rate, cardiac dysynchrony, activity, posture, blood chemistry, $0_2$ saturation, heart sounds, wall stress, wall strain, hypertrophy, inter-electrode impedance, electrical delays (PR interval, AV interval, QRS width, etc.), activity, cardiac chamber pressure, cardiac output, temperature, heart rate variability, depolarization amplitudes, depolarization timing, and/or other physiological parameters. It is contemplated that, in certain embodiments, information derived from such signals may be incorporated into the optimization algorithm that is employed to provide acute optimization of left ventricular preload in response varying CRT pacing parameters.

In some configurations, the implantable device 900 may incorporate one or more transthoracic impedance sensors that may be used to acquire the patient's respiratory waveform, and/or to acquire other respiratory-related information. The transthoracic impedance sensor may include, for example, one or more intracardiac electrodes 941, 942, 951-956 positioned in one or more chambers of the heart. The intracardiac electrodes 941, 942, 951-956 may be coupled to impedance drive/sense circuitry positioned within the housing 901 of the therapy device 900. Information from the transthoracic impedance sensor may be used to adapt the rate of pacing to correspond to the patient's activity or metabolic need, among other uses.

Communications circuitry is disposed within the housing 901 for facilitating communication between the CRM circuitry and a patient-external device, such as an external programmer or advanced patient management (APM) system. The communications circuitry may also facilitate unidirectional or bidirectional communication with one or more implanted, external, cutaneous, or subcutaneous physiologic or non-physiologic sensors, patient-input devices and/or information systems.

In certain embodiments, the therapy device 900 may include circuitry for detecting and treating cardiac tachyarrhythmia via defibrillation therapy and/or anti-tachyarrhythmia pacing (ATP). Configurations providing defibrillation capability may make use of defibrillation coils 941, 942 for delivering high energy shocks to the heart to terminate or mitigate tachyarrhythmia.

In some embodiments, the implantable therapy device 900 may include circuitry for selection of pacing electrode(s), timing sequence, and/or amplitude or pulse waveform output configurations (collectively referred to as pacing output configuration) to be applied via one or multiple electrodes within one or multiple heart chambers. For example, a pacing site evaluation procedure may be implemented to evaluate, after implant, an optimum pacing site to maximize ventricular preload. A change may be made in the timing parameters related to pacing (e.g., AV delay) to maximize ventricular preload. Any combination of pacemaker parameters may be used for both characterization of parameters to determine conditions of optimum preload, as well as for providing therapies using those parameters. For example, in a pacemaker equipped with multiple pacing electrodes respectively disposed at multiple pacing sites within a heart chamber, the ability to select one or more electrodes, temporal sequence, and/or pulse waveform characteristics for delivery of pacing can be used enhance the contractile function of the heart chamber by optimizing/maximizing ventricular preload.

Multi-site pacemakers, such as illustrated herein, are capable of delivering pacing pulses to multiple sites of the atria and/or ventricles during a cardiac cycle. Certain patients may benefit from activation of parts of a heart chamber, such as a ventricle, at different times in order to distribute the pumping load and/or depolarization sequence to different areas of the ventricle. A multi-site pacemaker has the capability of switching the output of pacing pulses between selected electrodes or groups of electrodes within a heart chamber during different cardiac cycles. For example, the pacing pulses may be delivered to the heart chamber at specified locations and at specified times during the cardiac cycle to enhance the synchrony of the contraction. Amplitude, pulse duration, a nodal/cathodal polarity and/or waveshape of the pacing pulses may also be altered to enhance pumping function as described hereinabove.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A medical system, comprising:
   one or more electrodes for delivering pacing pulses to a patient's heart;
   an energy delivery and sensing unit coupled to the one or more electrodes;
   a pulmonary artery pressure sensor capable of making pulmonary artery pressure measurements;
   a memory configured to store at least the pulmonary artery pressure measurements; and
   a controller coupled to the memory, the pulmonary artery pressure sensor, and the energy delivery and sensing unit, the controller configured to,
      vary, for each repetition of an acute burst protocol, a parameter of pacing applied to the patient's heart via the energy delivery and sensing unit during the acute burst protocol;
      store the pulmonary artery pressure measurements made during the repetitions of the acute burst protocol; and
      provide pacing therapy using a value of the parameter that is selected based on an optimum ventricular preload that is determined via the stored pulmonary artery pressure measurements;
   wherein a length of the repetitions is chosen so that the patient's baroreflex system does not adjust to the varied parameter of pacing during the repetitions of the acute burst protocol.

2. The medical system of claim 1, wherein the parameter of the pacing comprises a pacing delay.

3. The medical system of claim 1, wherein the parameter of the pacing comprises a pacing site of the electrodes.

4. The medical system of claim 1, wherein the controller is further configured to store the pulmonary artery pressure measurements between repetitions of the acute burst protocol to determine a baseline pulmonary artery pressure, and where the optimum ventricular preload is determined by comparing the baseline pulmonary artery pressure with the pulmonary artery pressure measurements stored during the repetitions of the acute burst protocol.

5. The medical system of claim 4, wherein the controller is configured to provide no pacing therapy during intervals between the repetitions of the acute burst protocol.

6. The medical system of claim 1, wherein the pulmonary artery pressure measurements comprise pulmonary artery diastolic pressure measurements.

7. The medical system of claim 1, wherein the controller is further configured to determine the optimum ventricular preload based on a maximum pressure measurement made during the repetitions of the acute burst protocol.

8. The medical system of claim 1, wherein the controller is further configured to provide the pacing therapy during ambulatory optimization of a pacing interval applied to the patient's heart.

9. The medical system of claim 1, wherein the parameter of the pacing comprises a combination of a pacing delay and a pacing site of the electrodes.

10. A medical system, comprising:
    means for applying pacing to a patient's heart for multiple repetitions of an acute burst protocol, wherein a parameter of the pacing is varied for each repetition of the acute burst protocol, and wherein a length of the repetitions is chosen so that the patient's baroreflex system does not adjust to the varied parameter of pacing during the repetitions of the acute burst protocol;
    means for measuring pulmonary artery pressure during the repetitions of the acute burst protocol;
    means for determining an optimum ventricular preload based on the measured pulmonary artery pressure; and
    means for providing pacing therapy using a value of the parameter of pacing that is selected based on the determination of optimum ventricular preload.

11. The medical system of claim 10, further comprising means for measuring the pulmonary artery pressure between repetitions of the acute burst protocol to determine a baseline pulmonary artery pressure, and wherein the means for determining the optimum ventricular preload further comprises means for comparing the baseline pulmonary artery pressure with the pulmonary artery pressure measured during the repetitions of the acute burst protocol.

12. The medical system of claim 10, wherein the parameter of the pacing comprises a pacing delay.

13. The medical system of claim 10, wherein the means for applying pacing comprises one or more electrodes, and wherein the parameter of the pacing comprises a pacing site of the electrodes.

14. The medical system of claim 10, wherein the means for applying pacing comprises one or more electrodes, and wherein the parameter of the pacing comprises a combination of a pacing delay and a pacing site of the electrodes.

15. The medical system of claim 11, wherein the means for measuring the pulmonary artery pressure between repetitions is configured to measure the pulmonary artery pressure with no pacing therapy applied.

* * * * *

UNITED STATES PATENT AND TRADEMARK OFFICE
CERTIFICATE OF CORRECTION

PATENT NO. : 7,957,802 B2
APPLICATION NO. : 11/894082
DATED : June 7, 2011
INVENTOR(S) : Patangay et al.

It is certified that error appears in the above-identified patent and that said Letters Patent is hereby corrected as shown below:

In the Specification:

Col. 11, line 60: "blood chemistry, O2" should read --blood chemistry, $O_2$--.

Signed and Sealed this
Eighteenth Day of October, 2011

David J. Kappos
*Director of the United States Patent and Trademark Office*